(12) United States Patent
Hsieh

(10) Patent No.: US 6,873,676 B2
(45) Date of Patent: Mar. 29, 2005

(54) CONVOLUTION RECONSTRUCTION ALGORITHM FOR MULTI-SLICE CT

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 195 days.

(21) Appl. No.: 10/379,971

(22) Filed: Mar. 5, 2003

(65) Prior Publication Data

US 2004/0174946 A1 Sep. 9, 2004

(51) Int. Cl.[7] .................................................. A61B 6/00
(52) U.S. Cl. ............................ 378/4; 378/15; 378/901
(58) Field of Search ............................... 378/4, 15, 901

(56) References Cited

U.S. PATENT DOCUMENTS

| 6,028,908 | A | 2/2000 | Taguchi | 378/15 |
|---|---|---|---|---|
| 6,028,909 | A | 2/2000 | Zmora | 378/15 |
| 6,185,271 | B1 | 2/2001 | Kinsinger | 378/19 |
| 6,275,562 | B1 | 8/2001 | He et al. | 378/19 |
| 6,381,297 | B1 * | 4/2002 | Hsieh | 378/15 |
| 6,385,279 | B1 | 5/2002 | Toth et al. | 378/11 |
| 6,452,996 | B1 * | 9/2002 | Hsieh | 378/15 |
| 6,529,576 | B2 * | 3/2003 | Hsieh et al. | 378/15 |

\* cited by examiner

Primary Examiner—David V. Bruce
Assistant Examiner—Courtney Thomas

(57) ABSTRACT

A multi-slice computed tomography imaging system (10) is provided including a source (18) generating a x-ray beam (32). A detector array (20) receives the x-ray beam (32) and generates projection data. A translating table (22) having an object (12) thereon is operable to translate in relation to the source (18) and the detector array (20). The source (18) and the detector array (20) rotate about the translating table (22) as to helically scan the object (12). An image reconstructor (44) is electrically coupled to the detector array (20). The reconstructor (44) determines a set of conjugate samples from the projection data and reconstructs an image by interpolating a set of projections corresponding to at least one plane of reconstruction in response to the set of conjugate samples, using convolutional scaling to produce a set of final weights. A method of reconstructing an image of an object for the imaging system (10) is also provided.

20 Claims, 3 Drawing Sheets

CONVOLUTION RECONSTRUCTION ALGORITHM FOR MULTI-SLICE CT

TECHNICAL FIELD

The present invention relates generally to multi-slice computed tomography (CT) imaging systems, and more particularly, to an apparatus and method of weighting parallel projections during image generation.

BACKGROUND OF THE INVENTION

A computed tomography (CT) imaging system typically, includes an x-ray source that projects a fan-shaped x-ray beam through an object being imaged, such as a patient to an array of radiation detectors. The beam is collimated to lie within an X-Y plane and generally referred to as the "imaging plane". Intensity of the attenuated beam radiation received at the detector array is dependent upon attenuation of the x-ray beam by the object. Attenuation measurements from each detector are acquired separately to produce a transmission profile.

The x-ray source and the detector array are rotated within a gantry and around the object to be imaged so that a projection angle at which the x-ray beam intersects the object constantly changes. A group of x-ray attenuation measurements, i.e., projection data, from the detector array at one gantry angle is referred to as a "view". A "scan" of the object comprises a set of views made at different projection angles, during one revolution of the x-ray source and detector array.

In an axial scan, the projection data is processed to construct an image that corresponds to a two-dimensional slice taken through the object. To reduce the total scan time required for multiple slices, a "helical" scan is performed. To perform a "helical" scan, the patient is moved along a z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reducing scan time, helical scanning provides other advantages such as better use of injected contrast, improved image reconstruction at arbitrary locations, and better three-dimensional images.

There is a continuous effort to increase computed tomography (CT) imaging system capabilities. CT imaging system imaging speeds are continuously increasing, as well as the number of detector rows. The increase in imaging speed allows physicians to gather CT images and constructions in a matter of seconds rather than several minutes as with previous CT imaging systems. Although the increase in imaging speed provides improved imaging capability, it causes new constraints and requirements for the functionality of the CT imaging systems.

Axial distance covered during one gantry rotation divided by slice thickness or detector row width, is referred to as helical pitch of the imaging system. For example, for a 6:1 helical pitch, the table of the CT imaging system travels six times a width of a detector row in a gantry rotation of $2\pi$. Therefore, it takes a gantry rotation of $2\pi/6$ or $\pi/3$ to travel a single detector row width. Therefore, angular span for each detector row is $\pi/3$ for a 6:1 helical pitch. In general when helical pitch increases, scan time decreases.

During an imaging sequence, projection data samples are taken from the detector array and weighted accordingly, followed by performing a filtered back projection technique. Weighting functions are applied to the projection data to effectively perform interpolation operation to compensate for object motion due to helical mode. The filtered back projection technique converts the attenuation measurements from a scan into integers called "CT numbers" or "Hounsfield units", which are used to control the brightness of a corresponding pixel on a cathode ray tube display.

There is a desire to increase the number of detector rows for a helical scan, in effect increasing the number of slices. When the number of detector rows are increased there is increased volume coverage of the scanned object and scanning time is decreased.

To overcome the above issues, various weighted distribution reconstruction algorithms have been applied to make it possible to reconstruct images from projection data scanned at helical pitches greater than 6:1. Unfortunately, existing reconstruction algorithms do not produce satisfactory images with an increased number of detector rows and increased helical pitches. When helical pitch is increased, angular span, the angular range of the projection samples of a single detector used for the reconstruction, is reduced. The shortened angular span increases the rate of change in the helical weights. This leads to streak or shading artifacts when scanning objects with significant variation along the patient long axis or z-axis.

It would therefore be desirable to provide a method of reconstructing an image for a multi-slice CT imaging system that has a high number of detector rows and helical pitches without creating streak or shading artifacts, while at the same time maintaining estimation accuracy of an image.

SUMMARY OF THE INVENTION

The present invention provides a method and apparatus for reconstructing an image of an object for a multi-slice computed tomography (CT) imaging system. A multi-slice CT imaging system is provided including a source generating a x-ray beam. A detector array receives the x-ray beam and generates projection data. A translating table having an object thereon is operable to translate in relation to the source and the detector array. The source and the detector array rotate about the translating table to helically scan the object. An image reconstructor is electrically coupled to the detector array. The image reconstructor determines a set of conjugate samples from the projection data and reconstructs an image by interpolating a set of projections corresponding to at least one plane of reconstruction in response to the set of conjugate samples, using convolutional scaling to produce a set of final weights. A method of reconstructing an image of an object for the multi-slice CT imaging system is also provided.

One of several advantages of the present invention is that it accommodates a larger number of detector rows. In so doing, it provides quicker helical scans.

Another advantage of the present invention is that it uses a convolutional approach, which minimizes cone beam and helical interpolation artifacts.

Furthermore, the present invention maintains the same amount of computation required in interpolation as previous weighted distribution reconstruction algorithms.

The present invention itself, together with attendant advantages, will be best understood by reference to the following detailed description, taken in conjunction with the accompanying figures.

BRIEF DESCRIPTION OF THE DRAWINGS

For a more complete understanding of this invention reference should now be had to the embodiments illustrated in greater detail in the accompanying figures and described below by way of examples of the invention wherein.

DETAILED DESCRIPTION OF THE PREFERRED EMBODIMENT

While the present invention is described with respect to method and apparatus for reconstructing an image of an object for a multi-slice computed tomography (CT) imaging system, the following apparatus and method is capable of being adapted for various purposes and is not limited to the following applications: MRI systems, CT systems, magnetic resonance spectroscopy systems, and other applications known in the art.

In the following description, various operating parameters and components are described for one constructed embodiment. These specific parameters and components are included as examples and are not meant to be limiting.

Also, in the following description low helical pitches are considered helical pitches that are less than the number of detector rows. For example, a 16-slice scanner with low helical pitch has helical pitches less than or equal to 15. High helical pitches are considered helical pitches equal to or greater than the number of detector rows.

Figure 1:
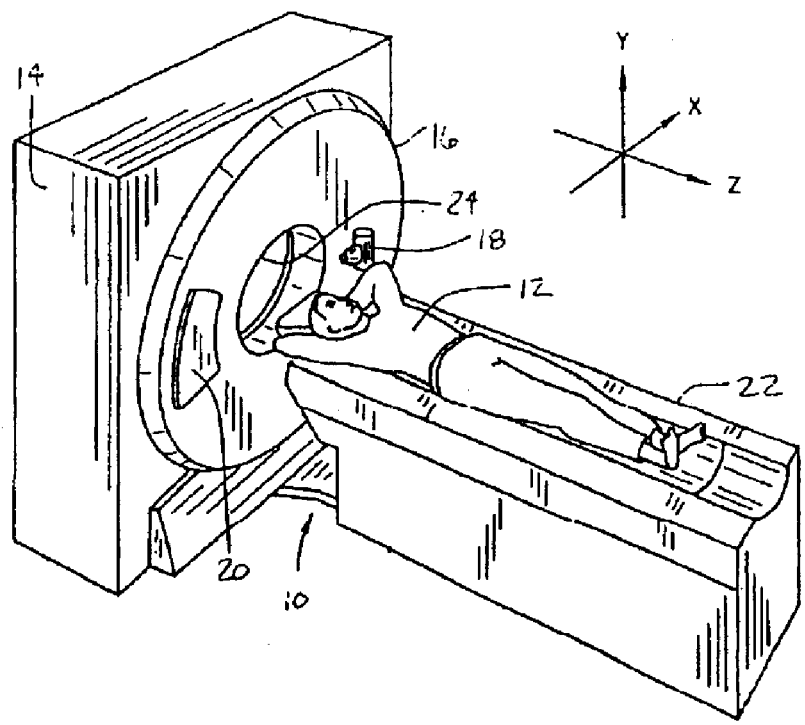
FIG. 1 is a pictorial view of a multi-slice CT imaging system utilizing a method of reconstructing an image in accordance with an embodiment of the present invention.

Referring now to FIG. 1, a pictorial view of a multi-slice CT imaging system 10, utilizing a method of reconstructing an image of medical patient 12 in accordance with an embodiment of the present invention, is shown. The imaging system 10 includes a gantry 14 that has a rotating inner portion 16 containing a x-ray source 18 and a detector array 20. The x-ray source 18 projects a beam of x-rays towards the detector array 20. The source 18 and the detector array 20 rotate about an operably translatable table 22. The table 22 is translated along a z-axis between the source 18 and the detector 20 to perform a helical scan. The beam, after passing through the medical patient 12, within a patient bore 24, is detected at the detector array 20 to generate projection data that is used to create a CT image.

Figure 2:
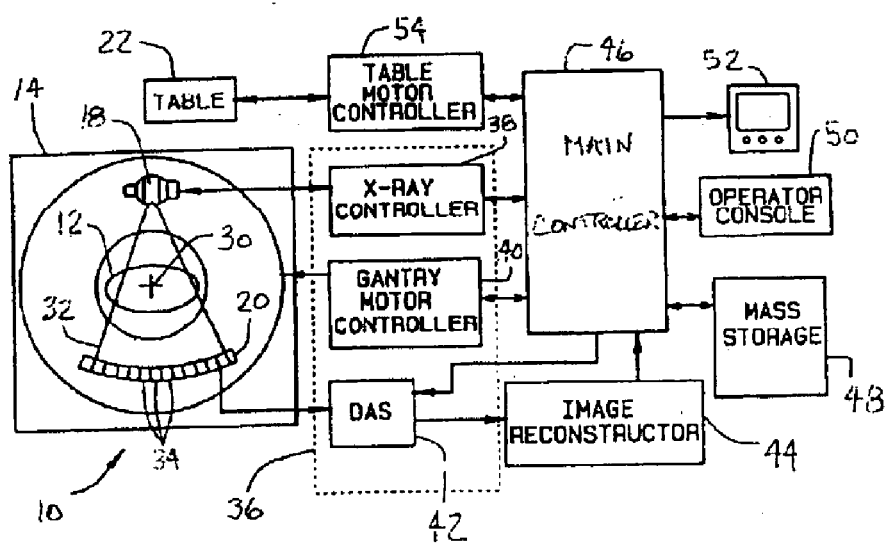
FIG. 2 is a block diagrammatic view of the multi-slice CT imaging system in accordance with an embodiment of the present invention.

Referring now to FIG. 2, a block diagrammatic view of the system 10 in accordance with an embodiment of the present invention, is shown. The source 18 and the detector array 20 rotate about a center axis 30. The beam 32 is received by multiple detector elements 34 in multiple detector rows. Each detector element 34 generates an electrical signal corresponding to intensity of an impinging x-ray beam. As the beam 32 passes through the patient 12 the beam 32 is attenuated. Rotation of gantry 14 and the operation of source 18 are governed by a control mechanism 36. Control mechanism 36 includes a x-ray controller 38 that provides power and timing signals to source 18 and a gantry motor controller 40 that controls the rotational speed and position of gantry 14. A data acquisition system (DAS) 42 samples analog data from the detector elements 34 and converts the analog data to digital signals for subsequent processing. An image reconstructor 44 receives sampled and digitized x-ray data from the DAS 42 and performs high-speed image reconstruction. A main controller 46 stores the CT image and projection data in a mass storage device 48.

The main controller 46 also receives commands and scanning parameters from an operator via an operator console 50. A display 52 allows the operator to observe the reconstructed image and other data from the main controller 46. The operator-supplied commands and parameters are used by the main controller 46 in operation of the DAS 42, the x-ray controller 38, and the gantry motor controller 40. In addition, the main controller 46 operates a table motor controller 54, which translates the table 22 to position patient 12 in gantry 14.

The x-ray controller 38, the gantry motor controller 40, the image reconstructor 44, the main controller 46, and the table motor controller 54 are preferably microprocessor-based such as a computer having a central processing unit, memory (RAM and/or ROM), and associated input and output buses. The x-ray controller 38, the gantry motor controller 40, the image reconstructor 44, the main controller 46, and the table motor controller 54 may be a portion of a central control unit or may each be stand-alone components as shown.

Figure 3:
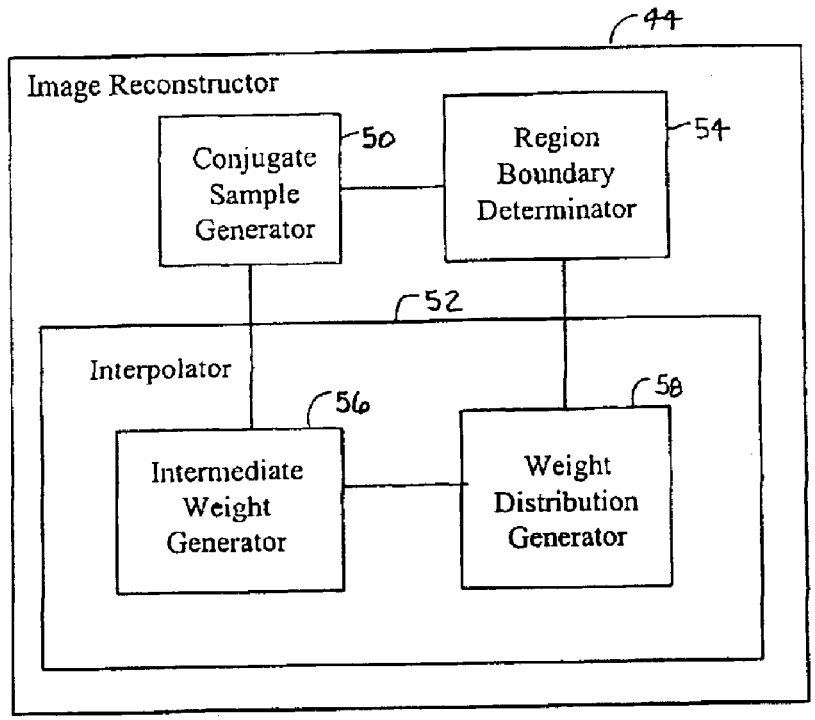
FIG. 3 is a block diagrammatic view of a image reconstructor in accordance with an embodiment of the present invention.
Figure 4:
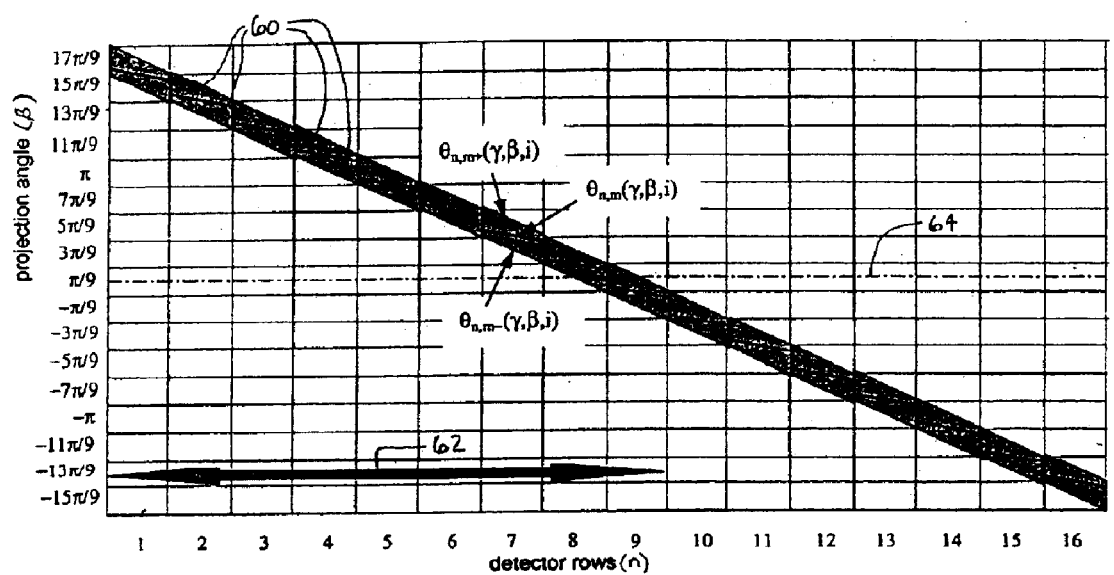
FIG. 4 is a plot illustrating conjugate weighting regions for a 16 row detector at 9:1 helical pitch utilizing the method of reconstructing an image in accordance with an embodiment of the present invention.

Referring now to FIG. 3, a block diagrammatic view of the image reconstructor 44 in accordance with an embodiment of the present invention, is shown. The reconstructor 44 includes a conjugate sample generator 50 that receives the projection data from the DAS 42 and determines a set of conjugate samples. A conjugate sample referring to a combined pair of samples, that are associated with a x-ray path. The conjugate sample generator 50 is coupled to an interpolator 52 and a region boundary determinator 54. The interpolator 52 includes an intermediate weight generator 56, which calculates weights to be given to the conjugate samples for respective detection angles γ, projection angles β, and detector rows i. The region boundary determinator 54 determines an upper boundary and a lower boundary for a pair of regions within a detector row, as best seen in FIG. 4 and further described below. A weight distribution generator 58, within the interpolator 52, is coupled to the region boundary determinator 54 and the intermediate weight generator 56. The weight distribution generator 58 calculates a final weight distribution for each of the pair of regions within each detector row.

Figure 5:
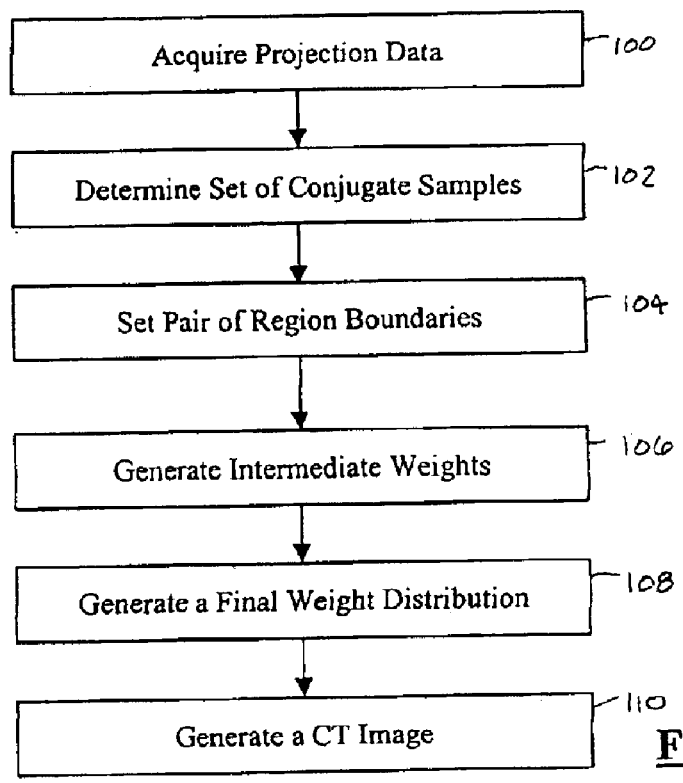
FIG. 5, is a logic flow diagram illustrating the method of reconstructing an image in accordance with an embodiment of the present invention.

Referring now to FIG. 5, a logic flow diagram illustrating the method of reconstructing a CT image in accordance with an embodiment of the present invention, is shown.

In step 100, the detector array 20 acquires projection data, using methods known in the art.

In step 102, the conjugate sample generator 50 determines a set of conjugate samples from the projection data, using methods known in the art.

In step 104, the region boundary determinator 54 sets a pair of region boundaries per detector row.

Referring now also to FIG. 4, a sample plot illustrating conjugate weighting regions for a 16-row detector at 9:1 helical pitch utilizing the method of reconstructing a CT image in accordance with an embodiment of the present invention, is shown. Nonzero weighted pairs of trapezoidally shaped regions 60 are shown for each detector row. Note for this example of low helical pitch, a minimum amount of projection samples needed for reconstruction corresponds to projections from nine detector rows or the number of detector rows k is equal to nine. The projection dataset is called a sub-dataset. The sub-dataset formed by detector row n to row n+k−1 is referred to as a sub-dataset n. A double arrow 62 depicts the detector row range to cover the sub-dataset n. The number of detector rows k changes with helical pitch. In general as helical pitch increases, k increases. When the gantry 14 rotates one revolution around the patient 12 the table 22 has translated along the z-axis a distance equal to a sum of 9 detector widths. In other words, angular span for each detector row is equal to $2\pi/9$.

A dashed horizontal line 64 at projection angle $\pi/9$ represents a conventional flat plane-of-reconstruction location, for a projected angle $\beta$ at which an iso-channel intersects the plane of reconstruction. The iso-channel is when the detector angle $\gamma$ is equal to zero. The plane of reconstruction is where a CT image is reconstructed. Note the present invention uses non-flat plane-of-reconstructions to reconstruct a CT image.

FIG. 4 is for example purposes only, any helical pitch p for any total number of detector rows N may be represented in a similar fashion.

In setting the pair of region boundaries the $m^{th}$ plane-of-reconstruction $\theta_{n,m}(\gamma,\beta,i)$, for a detector row i, is set equal to $\phi_{i,m} - \delta_m \gamma$, where $\phi_{i,m}$ is the projection angle at which the iso-channel of detector row i intersects the $m^{th}$ plane-of-reconstruction $\theta_{n,m}(\gamma,\beta,i)$. $\delta_m$ is a parameter that is determinative of slope of centerlines $\theta_{n,m}(\gamma,\beta,i)$ and boundary lines $\theta_{n,m-}(\gamma,\beta,i)$ and $\theta_{n,m+}(\gamma,\beta,i)$ and i=0, 1, ..., N−1.

$$\phi_{i,m} = \frac{2i\pi}{p} \quad (1)$$

When the centerlines $\theta_{n,m}(\gamma,\beta,i)$ are changed by altering $\delta_m$ the boundary lines $\theta_{n,m-}(\gamma,\beta,i)$ and $\theta_{n,m+}(\gamma,\beta,i)$ also change.

The lower boundaries $\theta_{n,m-}(\gamma,\beta,i)$ and upper boundaries $\theta_{n,m+}(\gamma,\beta,i)$ are independent of the sub-dataset n. For low helical pitch the lower boundaries $\theta_{n,m-}(\gamma,\beta,i)$ and upper boundaries, $\theta_{n,m+}(\gamma,\beta,i)$ may be described as follows:

$$\theta_{n,m-}(\gamma,\beta,i) = \phi_{i,m} - \frac{\pi}{p} - (2-\delta_m)\gamma, \text{ and} \quad (2)$$

$$\theta_{n,m+}(\gamma,\beta,i) = \phi_{i,m} + \frac{\pi}{p} - (2-\delta_m)\gamma \quad (3)$$

In a preferred embodiment of the present invention equations (2) and (3) are preferred for low odd numbered helical pitch scans so as to maximize quality of conjugate samples. Note that at odd helical pitches, the distance between conjugate samples for iso-channels is half of the distance between adjacent detector rows. For example, a 16-slice scanner may use any one of the following helical pitches: 1, 3, 5, 7, 9, 11, 13, or 15. The odd number helical pitches are helical pitch examples. Of course any number of helical pitch may be used.

For high helical pitch the lower boundaries $\theta_{n,m-}(\gamma,\beta,i)$ and upper boundaries $\theta_{n,m+}(\gamma,\beta,i)$ may be described as follows:

$$\begin{cases} \theta_{n,m-}(\gamma,\beta,i) = \phi_{i,m} - \frac{2\pi}{p} - (2-\delta_m)\gamma, & i=n \\ \theta_{n,m-}(\gamma,\beta,i) = \phi_{i,m} - \frac{2\pi}{p} - \delta_m\gamma, & n < i \le n+k-1 \end{cases} \quad (4)$$

and $$\begin{cases} \theta_{n,m+}(\gamma,\beta,i) = \phi_{i,m} + \frac{2\pi}{p} - (2-\delta_m)\gamma, & i=n+k-1 \\ \theta_{n,m+}(\gamma,\beta,i) = \phi_{i,m} + \frac{2\pi}{p} - \delta_m\gamma, & n \le i < n+k-1 \end{cases} \quad (5)$$

In a preferred embodiment of the present invention equations (4) and (5) are preferred for high even numbered helical pitch scans so as to maximize quality of conjugate samples. Note that since the helical pitch is larger than the number of detector rows, the use of the conjugate samples that are 180 degrees apart alone is insufficient to formulate a complete set of projections for reconstruction. Therefore, interpolation needs to be performed between adjacent rows as well as conjugate samples. For example, a 16-slice scanner may use any one of the following helical pitches: 16, 18, 20, 22, 24, 26, 28, and 30. The even number helical pitches are possible helical pitch examples. Of course any number of helical pitch may be used.

Since a majority of interpolation occurs between detector rows and conjugate interpolation is performed at end portions of the sub-dataset n, end-boundary definitions are different from other portions of the sub-dataset n, as indicated by two boundary equations for both equations (4) and (5). In equation (4), the boundary for i=n is different than the boundary for n<i<n+k−1. Similarly, equation (5) also depicts two boundaries. Also, both conjugate interpolation and row-to-row interpolation may be used for either low helical pitch applications or for high helical pitch applications. Although, a majority of weighting for high helical pitch is performed by row-to-row interpolation, portions of the intermediate weighting function are performed by conjugate interpolation. In general, conjugate interpolation produces better slice profile over row-to-row interpolation. Since, there exists less conjugate samples for high helical pitches, as known in the art, row-to-row interpolation is used in a higher proportion as compared to conjugate interpolation.

In step 106, the intermediate weight generator 58 calculates intermediate weights using an intermediate weight function $w_n(\gamma,\beta,i)$ that covers projections from detector rows n to n+k−1, where k is a minimum number of detector rows required to produce a complete set of projections. When there is N detector rows, the number of rows that are not utilized by a minimum dataset is N−k.

The intermediate weights are determined by the following intermediate weight function:

$$w_n(\gamma, \beta, i) = \begin{cases} \sum_{m=1}^{M} \dfrac{\lambda_{n,m}(\beta - \theta_{n,m-}(\gamma, \beta, i))}{\theta_{n,m}(\gamma, \beta, i) - \theta_{n,m-}(\gamma, \beta, i)}, & \theta_{n,m-}(\gamma, \beta, i) \le \beta < \theta_{n,m}(\gamma, \beta, i) \\ \sum_{m=1}^{M} \dfrac{\lambda_{n,m}(\theta_{n,m+}(\gamma, \beta, i) - \beta)}{\theta_{n,m+}(\gamma, \beta, i) - \theta_{n,m}(\gamma, \beta, i)}, & \theta_{n,m}(\gamma, \beta, i) \le \beta < \theta_{n,m+}(\gamma, \beta, i) \\ 0, & \text{otherwise} \end{cases} \quad (6)$$

where $\lambda_{n,m}$ is a scaling factor that indicates the weight for the $m^{th}$ plane-of-reconstruction and sub-dataset n. The total number of planes-of-reconstruction is equal to M. The intermediate weighting function $w_n(\gamma,\beta,i)$ by performing a summation over M provides an average over various slopes, which results in a smooth intermediate weighting function for each detector row.

The intermediate weighting function $w_n(\gamma,\beta,i)$ may be divided into two categories: a high helical pitch category and a low helical pitch category. High helical pitch is considered as the helical pitch p that is larger than or equal to the number of detector rows N. Similarly, a low helical pitch occurs when helical pitch p is less than the number of detector rows N. For low helical pitches, odd helical pitch aids in generating quality conjugate samples that are located less than one detector cell aperture apart. For high helical pitches, even helical pitch is preferred since typical interpolation is carried out on a row-to-row basis.

In step 108, the weight distribution generator calculates a final weight distribution using a final weight function:

$$\xi(\gamma, \beta, i) = \sum_{n=0}^{N-k} \alpha(n) w_n(\gamma, \beta, i) \quad (7)$$

The final weight distribution is the weighted summation of all the intermediate weights described by equation (6) multiplied by a convolutional scaling function $\alpha(n)$.

The convolutional scaling function $\alpha(n)$ has preferably a property of symmetry, such that $\alpha(n)=\alpha((N-k-n)$. The property of symmetry is due to the fact that the convolution scaling function is used to suppress cone beam artifacts by adjusting the contribution of different detector rows to the final reconstructed image. That is, projection samples with a large cone angle contribute less to a final image as compared to samples with a small cone angle. In a typical multi-slice scanner configuration, cone angles increase from center detector rows to peripheral rows and the cone angles are symmetrical. For example, for a 16-slice detector of the present invention, detector rows 1 and 16 have identical cone angles, which are larger than the cone angles of detector rows 2 and 15 and therefore contribute less to the final image. Detector rows 8 and 9 have minimum cone angle and contribute the most to the final image. The scaling function $\alpha(n)$ may be linear or nonlinear depending upon the application and desired result. For example the scaling function may be a Gaussian function as in the following equation (8):

$$\alpha(n) = e^{-(n-0.5(N-k))^2 \sigma^{-2}} \left( \sum_{m=0}^{N-k} e^{-(m-0.5(N-k))^2 \sigma^{-2}} \right)^{-1} \quad (8)$$

where n=0, 1, . . . , N−k and $\alpha$ is a parameter that specifies variation of a center detector row weight to outer detector row weights. Contribution of detector center rows are higher than contribution of detector outer rows, even with the use of the uniform scaling function $\alpha(n)$. By weighting the center detector rows higher than the outer detector rows cone beam artifacts are reduced.

In step 110, the reconstructor 44 utilizes the resulting weight distribution function to generate a CT image. One method for reconstructing a CT image from a set of projection data is referred to in the art as a filtered back projection technique. This process converts attenuation measurements from a scan into integers called "CT numbers" or "Hounsfield units", which are used to control brightness of a corresponding pixel on a cathode ray tube display. The filtered back projection technique performs differentiation to the weighted projections to generate the CT image. The present invention in providing a smooth resulting curve from the weight distribution function prevents artifacts normally created by the differentiation of sharp variations within a weighting function. Although, the present invention is described as using the filtered back projection technique other reconstruction techniques may be used, as known in the art to generate the CT image.

The above-described steps are meant to be an illustrative example, the steps may be performed synchronously or in a different order depending upon the application. Also, the above-described method provides a weighting function with minimum variations so as to minimize artifacts.

The present invention provides a multi-slice CT imaging system and method of reconstructing a CT image that minimizes helical interpolation artifacts and provides the ability for increased helical scanning speed. The present invention also provides versatility in that a system operator may select various helical pitches, number of detector rows, and reconstructuring filtering techniques depending upon the application to maximize image quality.

The above-described apparatus and manufacturing method, to one skilled in the art, is capable of being adapted for various purposes and is not limited to applications including MRI systems, CT systems, magnetic resonance spectroscopy systems, and other applications known in the art. The above-described invention can also be varied without deviating from the true scope of the invention.

What is claimed is:

1. A multi-slice computed tomography imaging system comprising:

a source generating a x-ray beam;

a detector array receiving said x-ray beam and generating projection data;

a translating table having an object thereon and operable to translate in relation to said source and said detector array;

said source and said detector array rotating about said translating table as to helically scan said object;

a image reconstructor electrically coupled to said detector array for determining a set of conjugate samples of said projection data and reconstructing an image by interpolating a set of projections corresponding to at least one plane of reconstruction in response to said set of conjugate samples using convolutional scaling to produce a set of final weights.

2. An imaging system as in claim 1 wherein said image reconstructor sets a pair of region boundaries and reconstructs said image by interpolating said set of projections wherein said set of projections are defined by said pair of region boundaries.

3. An imaging system as in claim 1 wherein said image reconstructor, in interpolating a set of projections, determines intermediate weights and a final weight distribution in response to said conjugate samples.

4. An imaging system as in claim 3 wherein said image reconstructor, in determining intermediate weights, applies an intermediate weighting function.

5. An imaging system as in claim 3 wherein said image reconstructor, in determining a final weight distribution, applies a final weighting function.

6. An imaging system as in claim 5 wherein said image reconstructor, in applying a final weighting function, utilizes a symmetrical scaling function.

7. An imaging system as in claim 6 wherein said image reconstructor, in utilizing a scaling function, utilizes a gaussian function.

8. An imaging system as in claim 5 wherein said final weighting function $\xi(\gamma,\beta,i)$ is equal to $$\sum_{n=0}^{N-k} \alpha(n) w_n(\gamma, \beta, i).$$

9. An imaging system as in claim 1 wherein an $m^{th}$ plane of reconstruction $\theta_{n,m}(\gamma,\beta,i)$ of said at least one plane of reconstruction for a detector row i is equal to $\phi_{i,m} - \delta_m \gamma$.

10. An imaging system as in claim 1 wherein said image reconstructor, in interpolating a set of projections, sets a lower boundary $\theta_{n,m-}(\gamma,\beta,i)$ equal to $$\phi_{i,m} - \frac{\pi}{p} - (2 - \delta_m)\gamma$$

and an upper boundary $\theta_{n,m+}(\gamma,\beta,i)$ equal to $$\phi_{i,m} + \frac{\pi}{p} - (2 - \delta_m)\gamma.$$

11. An imaging system as in claim 1 wherein said image reconstructor, in interpolating a set of projections, sets a lower boundary $\theta_{n,m-}(\gamma,\beta,i)$ as:

$$\begin{cases} \theta_{n,m-}(\gamma, \beta, i) = \phi_{i,m} - \frac{2\pi}{p} - (2 - \delta_m)\gamma, & i = n \\ \theta_{n,m-}(\gamma, \beta, i) = \phi_{i,m} - \frac{2\pi}{p} - \delta_m \gamma, & n < i \leq n + k - 1 \end{cases}$$

and an upper boundary $\theta_{n,m+}(\gamma,\beta,i)$ written as:

$$\begin{cases} \theta_{n,m+}(\gamma, \beta, i) = \phi_{i,m} + \frac{2\pi}{p} - (2 - \delta_m)\gamma, & i = n + k - 1 \\ \theta_{n,m+}(\gamma, \beta, i) = \phi_{i,m} + \frac{2\pi}{p} - \delta_m \gamma, & n \leq i < n + k - 1. \end{cases}$$

12. A method of reconstructing an image of an object for a multi-slice computed tomography imaging system comprising:
  helically scanning the object to acquire projection data;
  determining a set of conjugate samples of said projection data to create a set of projections;
  setting a pair of region boundaries; and
  reconstructing the image by interpolating said set of projections, within said pair of region boundaries, to produce projections corresponding to at least one plane of reconstruction using convolutional scaling to produce a set of final weights.

13. A method as in claim 12 wherein reconstructing the image by interpolating a set of projections comprises:
  weighting said set of projections in response to said conjugate samples comprising;
    determining intermediate weights by applying an intermediate weighting function; and
    determining a final weight distribution for said set of projections from a final weighting function.

14. A method as in claim 13 wherein said intermediate weighting function is written as:

$$w_n(\gamma, \beta, i) = \begin{cases} \sum_{m=1}^{M} \frac{\lambda_{n,m}(\beta - \theta_{n,m-}(\gamma, \beta, i))}{\theta_{n,m}(\gamma, \beta, i) - \theta_{n,m-}(\gamma, \beta, i)}, & \theta_{n,m-}(\gamma, \beta, i) \leq \beta < \theta_{n,m}(\gamma, \beta, i) \\ \sum_{m=1}^{M} \frac{\lambda_{n,m}(\theta_{n,m+}(\gamma, \beta, i) - \beta)}{\theta_{n,m+}(\gamma, \beta, i) - \theta_{n,m}(\gamma, \beta, i)}, & \theta_{n,m}(\gamma, \beta, i) \leq \beta < \theta_{n,m+}(\gamma, \beta, i) \\ 0, & \text{otherwise} \end{cases}$$

15. A method as in claim 13 wherein said final weighting function $\xi(\gamma,\beta,i)$ is equal to $$\sum_{n=0}^{N-k} \alpha(n) w_n(\gamma, \beta, i).$$

16. A method as in claim 12 wherein a $m^{th}$ plane of reconstruction $\theta_{n,m}(\gamma,\beta,i)$ of said at least one plane of reconstruction for a detector row i is equal to $\phi_{i,m} - \delta_m \gamma$.

17. A method as in claim 12 wherein interpolating a set of projections comprises setting a lower boundary $\theta_{n,m-}(\gamma,\beta,i)$ equal to $$\phi_{i,m} - \frac{\pi}{p} - (2 - \delta_m)\gamma$$

and setting an upper boundary $\theta_{n,m+}(\gamma,\beta,i)$ equal to $$\phi_{i,m} + \frac{\pi}{p} - (2 - \delta_m)\gamma.$$

18. A method as in claim 7 wherein said lower boundary and said upper boundary are for odd numbered helical pitches.

19. A method as in claim 12 wherein interpolating a set of projections comprises setting a lower boundary $\theta_{n,m-}(\gamma,\beta,i)$ as follows:

$$\begin{cases} \theta_{n,m-}(\gamma, \beta, i) = \phi_{i,m} - \frac{2\pi}{p} - (2 - \delta_m)\gamma, & i = n \\ \theta_{n,m-}(\gamma, \beta, i) = \phi_{i,m} - \frac{2\pi}{p} - \delta_m \gamma, & n < i \leq n + k - 1 \end{cases}$$

and setting an upper boundary $\theta_{n,m+}(\gamma,\beta,i)$ as follows:

$$\begin{cases} \theta_{n,m+}(\gamma, \beta, i) = \phi_{i,m} + \frac{2\pi}{p} - (2-\delta_m)\gamma, & i = n+k-1 \\ \theta_{n,m+}(\gamma, \beta, i) = \phi_{i,m} + \frac{2\pi}{p} - \delta_m\gamma, & n \le i < n+k-1. \end{cases}$$

20. A method as in claim 19 wherein a second lower boundary $\theta_{n,m-}$ and a second upper boundary $\theta_{n,m+}$ are for even numbered helical pitches.

* * * * *

UNITED STATES PATENT AND TRADEMARK OFFICE
CERTIFICATE OF CORRECTION

PATENT NO. : 6,873,676 B2  Page 1 of 1
APPLICATION NO. : 10/379971
DATED : March 29, 2005
INVENTOR(S) : Jiang Hsieh It is certified that error appears in the above-identified patent and that said Letters Patent is hereby corrected as shown below:

Column 10, line 53, should read as follows:

-- 18. A method as in claim 17 wherein said lower boundary --

Signed and Sealed this

Nineteenth Day of September, 2006

JON W. DUDAS
*Director of the United States Patent and Trademark Office*